United States Patent [19]

Lekholm et al.

[11] Patent Number: 5,076,271

[45] Date of Patent: Dec. 31, 1991

[54] RATE-RESPONSIVE PACING METHOD AND SYSTEM EMPLOYING MINIMUM BLOOD OXYGEN SATURATION AS A CONTROL PARAMETER AND AS A PHYSICAL ACTIVITY INDICATOR

[75] Inventors: Anders Lekholm, Northridge, Calif.; Roland Heinze, Munich, Fed. Rep. of Germany

[73] Assignee: Siemens-Pacesetter, Inc., Sylmar, Calif.

[21] Appl. No.: 555,965

[22] Filed: Jul. 19, 1990

[51] Int. Cl.$^5$ .............................................. A61N 1/305
[52] U.S. Cl. ............................................... 128/419 PG
[58] Field of Search ........................................ 128/419

[56] References Cited

U.S. PATENT DOCUMENTS

| | | | |
|---|---|---|---|
| 3,596,252 | 6/1986 | Nelson | 128/419 PG |
| 4,140,132 | 2/1979 | Dahl | 128/419 PG |
| 4,202,339 | 5/1980 | Wirtzfeld et al. | 28/419 PG |
| 4,232,679 | 11/1980 | Schulman | 128/419 PG |
| 4,399,820 | 3/1983 | Wirtzfeld et al. | 128/419 PG |
| 4,485,813 | 12/1984 | Anderson et al. | 128/675 |
| 4,596,251 | 6/1986 | Plicchi et al. | 128/419 PG |
| 4,712,555 | 12/1987 | Thornander et al. | 128/419 PG |
| 4,815,469 | 3/1989 | Cohen et al. | 128/634 |
| 4,856,523 | 8/1989 | Sholder et al. | 128/419 PG |
| 4,870,968 | 10/1989 | Wiertzfeld | 128/419 PG |

OTHER PUBLICATIONS

Stangl et al., "A New Multisensor Pacing System Using Stoke Volume, Respiratory Rate, Mixed Venous Oxygen Saturation, and Temperature, Right Atrial Pressure, Right Ventricular Pressure and dP/dt", *Pace*, vol. 11, pp. 712-724 (Jun. 1988).

Furman et al., *A Practice of Cardiac Pacing*, Chapter 2, (Futura Publishing Co., Mt. Kisco, N.Y. 1986).

Moses et al., *A Practical Guide to Cardiac Pacing*, Chapter 8, (Little, Brown & Co., Boston/Toronto 1983).

*Primary Examiner*—William E. Kamm
*Attorney, Agent, or Firm*—Bryant R. Gold; Malcolm J. Romano

[57] ABSTRACT

A rate-responsive pacing method and system senses the minimum blood oxygen saturation in the right atrium of a patient's heart and uses such minimum blood oxygen saturation as a control parameter for indicating the muscular activity of a patient. Because the oxygen content of the venous blood in the right atrium varies significantly as venous blood from all parts of the body is introduced therein, evidencing differing levels of oxygen demand throughout the patient's body, the minimum oxygen content of the venous blood provides an accurate and reliable measure of those portions of the patient's body experiencing the greatest oxygen demand, i.e., experiencing muscular activity. A rate-responsive pacing system includes means for sensing the minimum oxygen content in the right atrium over a prescribed time interval, and using such minimum oxygen content as a control parameter for adjusting the rate of the pacemaker.

18 Claims, 4 Drawing Sheets

RATE-RESPONSIVE PACING METHOD AND SYSTEM EMPLOYING MINIMUM BLOOD OXYGEN SATURATION AS A CONTROL PARAMETER AND AS A PHYSICAL ACTIVITY INDICATOR

BACKGROUND OF THE INVENTION

The present invention relates to rate-responsive pacing methods and systems, and more particularly to a rate-responsive pacing method or system wherein the minimum oxygen saturation level of the venous blood in the right atrium is used as a control parameter to adjust the rate at which electrical stimulation pulses are delivered to a patient's heart.

A pacemaker is a medical device, usually an implantable medical device, that provides electrical stimulation pulses to a patient's heart at a controlled rate for the purpose of controlling the heart rate. Most modern implantable pacemakers can be programmed to operate in several modes, as required by the needs of a particular patient. Several common modes of operation provide stimulation pulses only when the patient's heart does not beat by itself at a minimum rate. In such mode(s), the stimulation pulses are provided only when needed, or "on demand", thereby preserving the limited power source of the implanted pacemaker for the longest possible time. Typically, the manner in which such demand pacemakers operate is to define a basic pacing interval (sometimes referred to as an "escape interval") and to wait and see if the heart beats during this interval. (A heart beat is determined by sensing a "P-Wave" indicating contraction of the atria, or an "R-wave", indicating contraction of the ventricles.) If so, the basic pacing interval starts over, and no stimulation pulse is provided. If not, a stimulation pulse is provided at the end of the pacing interval. In this manner, the pacemaker's pacing interval defines the rate at which stimulation pulses are provided to the heart in the absence of naturally occurring heart beats. It is noted that pacemakers may be employed that stimulate either, or both, chambers of the heart (i.e., either the right atrium and/or the right ventricle).

A rate-responsive pacemaker is a pacemaker that automatically adjusts the pacing interval, or the rate at which stimulation pulses are provided to the patient's heart, as a function of the sensed physiological needs of the patient. That is, every person has times when his or her heart needs to beat fast, and times when his or her heart should beat slow. For example, physical activity causes a person's heart rate to increase in order to compensate for the increased oxygen demands of the muscle tissue undergoing the physical activity. Similarly, physical inactivity, such as prolonged periods of sleep or rest, allow a person's heart rate to decrease because the oxygen demands of the body tissue are less. A rate-responsive pacemaker thus attempts to sense the physiological needs of a patient at a particular time, e.g., by sensing physical activity or inactivity, and adjusts the pacing interval of the pacemaker accordingly.

The operation and design of pacemakers, including rate-responsive pacemakers, are known in the art. See, e.g., Furman, et al., *A Practice of Cardiac Pacing*, (Futura Publishing Co., Mt. Kisco, N.Y. 1986); Moses, et al., *A Practical Guide to Cardiac Pacing* (Little, Brown & Co., Boston/Toronto 1983); U.S. Pat. No. 4,712,555 (Thornander et al); U.S. Pat. No. 4,856,523 (Sholder et al). U.S. Pat. No. 4,712,555 (Thornander et al.) is a particularly comprehensive reference explaining the general operation of a rate-responsive pacemaker, and the application of one particular type of physiological parameter (a timing interval) for controlling such pacemaker. U.S. Pat. No. 4,712,555 is incorporated herein by reference. Further, it is known in the art to sense several different physiological parameters as the control parameter of a rate-responsive pacemaker. One common type of sensor is an activity sensor that senses the physical activity level of the patient. See, e.g., U.S. Pat. No. 4,140,132, issued to Dahl; and U.S. Pat. No. 4,485,813, issued to Anderson.

Other types of sensors used in prior art rate-responsive pacers include sensors that sense respiration rate, blood and/or body temperature, blood pressure, the length of the Q-T interval, and the length of the P-R interval.

Of particular significance to the present invention, it is also known in the art to use an implantable sensor to determine the oxygen content of blood and to use such sensor in a rate-responsive pacemaker. See, e.g., U.S. Pat. Nos. 4,202,339; 4,399,820; and 4,815,469. Further, recent studies have suggested that mixed venous oxygen saturation provides one of the best indications available of physiological need, especially for low and medium levels of exercise (physical activity). It has thus been suggested that mixed venous oxygen saturation, when combined with other parameters, provides a very useful control parameter for controlling a rate-responsive pacemaker. See, Stangl, et al., "A New Multisensor Pacing System Using Stroke Volume, Respiratory Rate, Mixed Venous Oxygen Saturation, and Temperature, Right Atrial Pressure, Right Ventricular Pressure and dP/dt," PACE, Vol. 11, pp 712-724 (June 1988).

Unfortunately, while oxygen saturation may be one of the most sensitive parameters to indicate low and medium level exercise, the techniques heretofore used in the prior art to sense oxygen saturation have masked out the most beneficial information provided by this parameter. For example, oxygen saturation is typically sensed optically using a sensor that includes both a source of light, such as a light emitting diode (LED), and a means for detecting light, such as a phototransistor. The sensor, including both LED and phototransistor, is positioned in an appropriate location to sense venous oxygen saturation, e.g., in the right atrium. Light energy is directed to the blood in the right atrium from the light source. The amount of light energy reflected back to the phototransistor is a function of the properties of the blood, including the level of oxygen saturation of the blood. Thus, by monitoring the ratio of emitted light energy to reflected light energy, it is possible to measure the blood oxygen saturation level of the blood in the right atrium. However, because the return blood in the right atrium comes from all parts of the body, it contains significantly different levels of blood oxygen saturation, reflecting the different activity levels of various parts of the body. That is, if the patient is walking, the blood returned from the legs and arms (assuming the arms are swinging as the legs are walking) will have a significantly lower oxygen content than will blood from other parts of the body. This is because the leg and arm muscle tissue is working harder (and therefore consuming more oxygen) than is muscle tissue at other body locations.

Hence, the blood oxygen saturation measured in the right atrium tends to fluctuate over a wide range, depending upon how thoroughly the blood is mixed at the time the measurement is made. To compensate for these fluctuations, the prior art teaches averaging or integrating the measurement over a sufficiently long period of time to smooth out such fluctuations. Disadvantageously, such averaging or integrating masks out the most beneficial portions of the measurement—the oxygen saturation level of the blood returned from the arms and legs, or other parts of the body that are experiencing physical activity. What is needed, therefore, is a technique or method for measuring the oxygen saturation of the blood returned from just those portions of the body undergoing the greatest physical activity, or otherwise isolating that portion of the fluctuating oxygen saturation measurement indicative of such physical activity.

Further, when measuring blood oxygen saturation using an optical sensor that measures reflected light energy, and when such sensor is positioned in the heart, the amount of reflected light energy detected by such sensor is significantly influenced by optical reflections from the heart wall or valves. Such optical reflections disadvantageously give erroneously high readings. Hence, what is needed is a sensing method or system that senses only those optical reflections from returned blood, not from optical reflections occurring within the heart. More particularly, what is needed is a system and method for sensing optical reflections from blood returned to the heart from only those body portions undergoing the most strenuous physical activity.

The present invention advantageously provides a system and method of blood oxygen saturation measurement that addresses the above and other needs.

SUMMARY OF THE INVENTION

In accordance with one aspect of the present invention, a rate-responsive pacing method senses the minimum blood oxygen saturation level of the venous blood in the right atrium of a heart, and uses such minimum blood oxygen saturation level as a control parameter for indicating the muscular activity of a patient. As mentioned above, the oxygen content of the venous blood in the right atrium varies significantly as venous blood from all parts of the body returns thereto, but is not thoroughly mixed therein. Some of the venous blood exhibits a low oxygen content when returned from insulated parts of the body, such as the arms or legs, undergoing muscular activity. Other of the venous blood, from parts of the body not experiencing significant muscular activity, exhibits a higher blood oxygen content. Advantageously, the minimum oxygen content of the poorly mixed venous blood in the right atrium thus provides an accurate and reliable measure of muscular activity used by the pacing method of the present invention to adjust the rate at which pacing pulses are provided on demand to the patient.

In accordance with another aspect of the present invention, a rate-responsive pacing system is provided that includes an implanted rate-responsive pacemaker coupled to an appropriate chamber(s) of the patient's heart. A blood oxygen sensor, e.g., a sensor that optically senses the oxygen content of the blood in contact therewith, is positioned so as to sense the oxygen content of the poorly mixed venous blood in the right atrium. Preferably, this oxygen sensor forms an integral part of the pacing lead that couples the rate-responsive pacemaker with the heart. The minimum oxygen content thus sensed is used as a control parameter to automatically adjust the pacing rate of the rate-responsive pacemaker, i.e., to automatically adjust the rate at which pacing or stimulation pulses are provided on demand by the pacemaker in order to meet the physiologic needs of the patient.

An optical sensor is preferably used with the present invention to sense the oxygen content of the venous blood in the right atrium. Advantageously, when this is done, the minimum oxygen content thus sensed automatically rejects any erroneous high readings caused by optical reflections within the heart.

One embodiment of the present invention may thus be characterized as a method of automatically controlling the rate at which a rate-responsive pacemaker delivers pacing pulses to a patient's heart. Such method comprises: (a) measuring the oxygen content of the blood in the right atrium of the patient's heart; (b) determining the minimum value of blood oxygen content measured in step (a) during a prescribed time period; and (c) using the minimum value of blood oxygen content determined in step (b) as a control parameter to adjust the pacing rate of the rate-responsive pacemaker.

Another embodiment of the invention may be characterized as simply a method or system of determining the relative physical activity level of a patient. Such method or system includes the steps of or means for: (a) repeatedly measuring the oxygen content of venous blood in the patient; (b) monitoring the measurements made in step (a) over a prescribed interval; (c) ascertaining the minimum blood oxygen content measured during the monitoring interval of step (b); and (d) using the minimum blood oxygen content ascertained in step (c) as an indication of the physical activity level of the patient, where a greater physical activity is indicated by a lower minimum blood oxygen content.

A preferred rate-responsive pacing system in accordance with the present invention includes: (1) a blood oxygen sensor, this sensor including light emitting means for emitting light energy therefrom, and light sensing means for sensing light energy directed thereto; (2) a sensor drive circuit for selectively causing the light emitting means to emit light energy; (3) a sensor process circuit for determining the amount of light energy sensed by the light sensing means corresponding to a given amount of light emitted by the light emitting means, and for converting the determined amount of light energy into a first measurement representative of the minimum amount of light energy sensed during a prescribed interval; (4) rate-responsive pacing means for generating stimulation pulses on demand at a rate controlled by the first measurement; and (5) lead means for delivering the stimulation pulses to a desired heart chamber.

It is a feature of the present invention to provide an accurate and reliable system and/or method for determining the oxygen content of venous blood using optical measuring techniques, i.e., emitting light energy into the blood and sensing the amount of light energy reflected therefrom, despite reflections and other erroneous light energy sensings that may occur.

It is another feature of the invention to provide a reliable and accurate system and/or method for measuring the oxygen content of blood returning from body tissue undergoing the greatest oxygen demand, e.g., experiencing the most physical exercise, even though such blood is in the process of being mixed with blood returning from body tissue not experiencing a high oxygen demand. In other words, it is a feature of the present invention to provide a system and/or method that sorts relevant blood oxygen measurements (i.e., from blood returning from active body tissue) from irrelevant blood oxygen measurements (i.e., from blood returning from non-active body tissue).

It is a further feature of the invention to provide such a system and/or method for measuring relevant blood oxygen levels that can be used as a control parameter in a rate-responsive pacing system.

It is yet another feature of the invention to provide a rate-responsive pacing system and/or method wherein stimulation pulses may be provided to a patient's heart on demand at a rate that is determined by the oxygen content of blood returning from those parts of the patient's body experiencing the greatest oxygen demand.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

Figure 1:
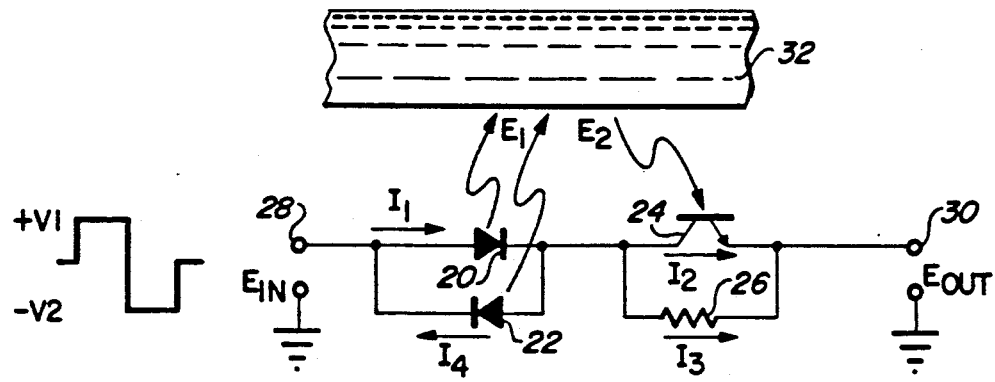
FIG. 1 is a schematic diagram of an optical blood oxygen sensor of the prior art.

The following description is of the best mode presently contemplated for carrying out the invention. This description is not to be taken in a limiting sense, but is made merely for the purpose of describing the general principles of the invention. The scope of the invention should be determined with reference to the claims.

It is noted that in accordance with one aspect of the present invention, a rate-responsive pacing system is provided in which the oxygen content of blood is used as a physiological parameter to control the rate at which stimulation pulses are provided to a heart of a patient. As previously indicated, rate-responsive pacing systems are known and described in the art, and will not be described in any detail herein. While such systems take several forms, all employ some means for sensing one or more physiological parameters of the patient indicative of how fast or slow the patient's heart should beat. The present invention is directed primarily to the manner in which the oxygen content of blood can be accurately measured, and once measured, used as a physiological parameter for controlling a rate-responsive pacing system.

In order to better appreciate the advantages associated with the use of the present invention, it will first be helpful to have a basic understanding of the manner in which oxygen content of blood is sensed. Accordingly, reference is made to FIG. 1, where there is shown a schematic diagram of an optical blood oxygen sensor of the prior art. The sensor includes two light-emitting diodes 20 and 22 connected in parallel, with the anode of diode 20 being connected to the cathode of diode 22, and the anode of diode 22 being connected to the cathode of diode 20. A phototransistor 24 is connected in parallel with a resistor 26, and the collector of the phototransistor 24 is connected to the same node as is the anode of diode 22 and the cathode of diode 20. The node comprising the anode of diode 20 and the cathode of diode 22 comprises one input terminal 28, and the emitter of phototransistor 24 and one side of the resistor 26 comprises another terminal of the sensor 30.

In operation, a bi-phase voltage pulse is applied across terminals 28 and 30. This bi-phase voltage pulse is also illustrated in FIG. 1 and includes a positive portion, having an amplitude of $+V1$; followed by a negative portion, having a negative amplitude of $-V2$. The positive portion of the bi-phase voltage pulse causes a current I1 to flow through light-emitting diode 20, thereby causing light energy E1 to be emitted by the LED 20. The light E1 comes in contact with a desired body fluid 32, such as blood. Depending upon the properties of the fluid 32, a portion of the light energy E1 is reflected back to the phototransistor 24. In FIG. 1, as well as in the other figures, that portion of light energy reflected back to the phototransistor is identified as E2. Thus, in FIG. the amount of current I2 that flows through phototransistor 24 is a function of the light energy E2 that is incident upon the base of the phototransistor 24. The balance of the current I1 that does not flow through phototransistor 24, therefore, flows through the resistor 26. This current is identified as I3. Thus, it is seen that I1 is equal to I2 and I3. The current I2 varies as a function of the light energy E2, thereby also affecting the amount of current I3 that flows through resistor 26. The voltage developed across terminals 28 and 30 (which voltage is a function of the forward drop across LED 20 and the voltage drop across resister 26 caused by the current flow I3) will thus vary as a function of the reflected light energy E2 that is incident upon the phototransistor 24. Hence, by monitoring the voltage across the terminals 28 and 30, it is possible to get an indication of the reflectance properties of the fluid 32.

In order to determine the amount of voltage variation across terminals 28 and 30 caused by the current I2, it is necessary to isolate other variations in this voltage from the measurement. This is typically done by causing current I4 to flow through resistor 26 and LED 22 during the negative portion of the bi-phase voltage waveform. During this portion of the waveform, both the phototransistor 24 and LED 20 are back biased, and therefore no current flows through either of these devices. The value of I4 is selected to be close to the value of I1 so that the forward voltage drop across LED 20 will be approximately the same as the forward voltage drop across LED 22.

Because of some of the difficulties associated with using and operating the prior art sensor shown in FIG. 1, an improved blood oxygen sensor has been proposed as disclosed in U.S. Pat. No. 4,815,469, which patent is incorporated herein by reference. While the sensor described in the '469 patent, or one equivalent thereto, is the preferred type of sensor for use with the present invention, it is to be emphasized that any type of sensor capable of sensing the oxygen content of blood may be used with the methods and systems of the present invention.

Figure 2:
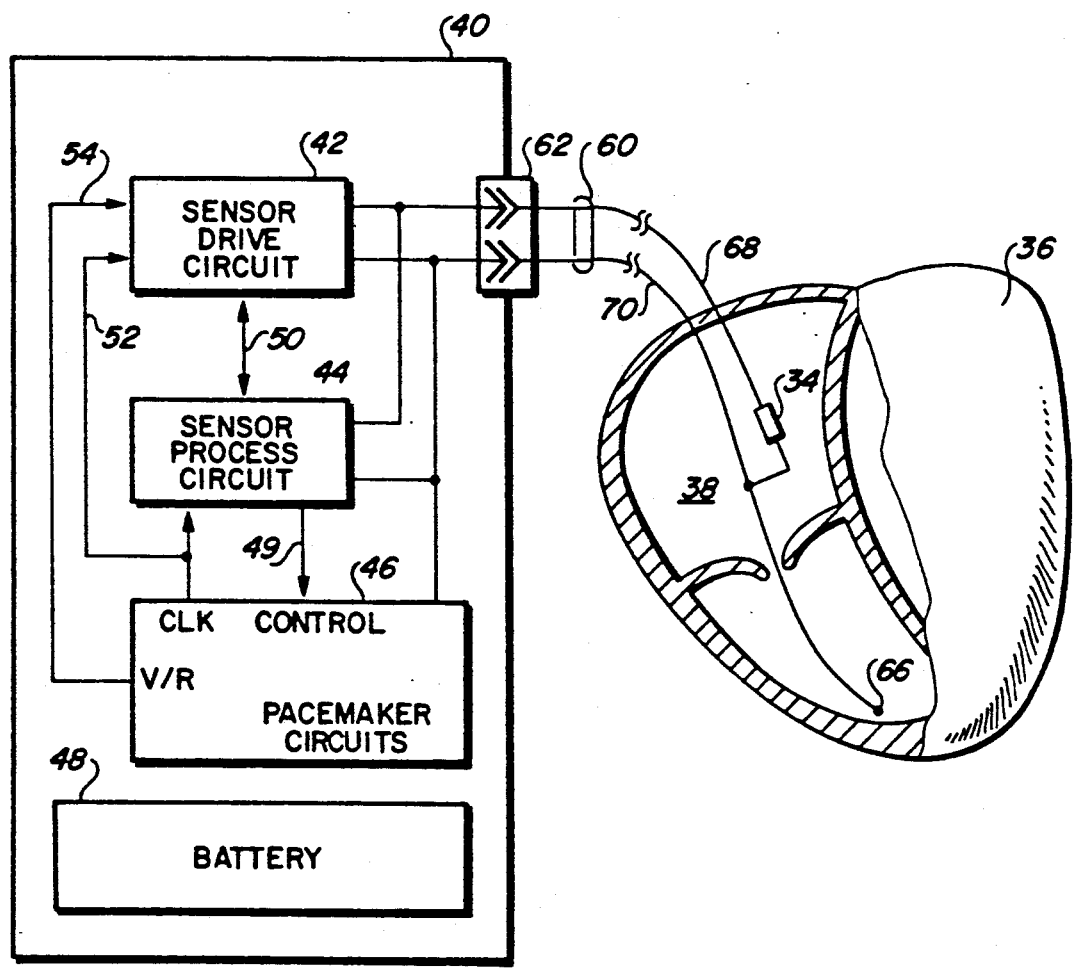
FIG. 2 is a block diagram depicting a blood oxygen sensor used in a rate-responsive pacing system.

Referring next to FIG. 2, there is shown a block diagram depicting a preferred manner of using a blood oxygen sensor 34 (such as the sensor described in the '469 patent), in a rate-responsive pacing system. The sensor 34 is positioned within an area of a patient's body where venous blood is able to come in contact with light energy E! emitted by the sensor. The preferred placement of the sensor is within a heart 36 of the patient, and more particularly within the right atrium 38 of the heart 36. An implantable rate-responsive pacemaker 40 is implanted in the patient in conventional manner. Included within the implantable pacemaker 40 is a sensor drive circuit 42, a sensor process circuit 44, and conventional rate-responsive pacemaker circuits 46. Also included in the pacemaker 40 is a source of electrical energy, e.g., a battery 48.

The drive circuit 42 provides the drive voltage necessary for operation of the sensor 34. The sensor process circuit 44, senses the returning signal from the sensor, e.g. the voltage potential at the output of the sensor 34, in response to an applied drive voltage. As is known in the art, and as described in the '469 patent, this sensor output voltage varies as a function of the oxygen content of the blood from which the emitted light energy is reflected. Hence, by monitoring changes in this output voltage, a qualitative measurement of the oxygen content of the blood may be made. By using appropriate calibration techniques, a quantitative measurement of the oxygen content of the blood may be made.

The drive circuit 42 and the sensor circuit 44 are coupled to each other and to the pacemaker circuits 46. Appropriate timing signals 50 are shared between the sensor drive circuit 42 and the sensor process circuit 44. Such timing signals assure that both circuits operate only at a desired time within the cardiac cycle or other control cycle. (The "cardiac cycle" is the time required by the heart 36 to complete one beat. This cycle is typically manifest by contraction or depolarization of the atria, evidenced by the generation of a P-wave, followed by contraction or depolarization of the ventricles, evidenced by the generation of an R-wave. P-waves and R-waves are evident by examining the patient's electrocardiogram, or ECG. The cardiac cycle is frequently measured from R-wave to R-wave, as the R-wave is the predominant wave, and thus the easiest to measure, in the ECG.) Further, in order to synchronize the sensing function of the sensor 34 with other events associated with the operation of the pacemaker circuits 46, the sensor drive circuit 42 and the sensor process circuit 44 receive a clock signal 52 and a timing reference signal 54 from the pacemaker circuits 46. Thus, for example, the timing reference signal 54 may be a signal indicating a cardiac event, such as a V-pulse or an R-wave signal, which signals indicate that the ventricle of the heart has either been paced (meaning that a stimulation pulse, e.g. a ventricular stimulation pulse, or V-pulse, has been provided by the pacemaker), or that a ventricular contraction, an R-wave, has been sensed.

In operation, the clock signal 52, as well as a timing reference signal, such as a V/R signal, are provided from the pacemaker circuit 46 to the sensor drive circuit 42 and the sensor process circuit 44. A pacing lead 60, connected to the pacemaker 40 by way of, e.g., a conventional bipolar pacer connector 62, allows the pacemaker to deliver stimulation pulses to the heart 36 at a distal electrode tip 66 through conductor 70. This same conductor 70 allows the pacemaker circuits 46 to sense cardiac events occurring near the lead tip 66.

In a preferred embodiment, the sensor 34 is advantageously embedded within the pacemaker lead 60 at a location near the distal tip so as to place the sensor 34 in the right atrium 38 of the heart 36. Further, when positioned properly within the heart, the lead is formed in a manner that causes the sensor 34 to face blood (and therefore measure the oxygen content of blood) just after the blood enters the atrium 38, before such blood has an opportunity to become thoroughly mixed within the atrium. One terminal of the sensor 34 is connected to a separate conductor 68 of the lead 60. The other terminal of the sensor 34 is connected within the lead to the conductor 70.

The sensor process circuit 44 develops a control signal 49 that is representative of the reflectance properties of the blood (and hence relatable to the amount of oxygen within the blood). This control signal 49 is presented to the pacemaker circuits 46 and is used as a physiological parameter to control the rate at which the pacemaker circuits deliver a stimulation pulse to the heart.

Figure 3A:
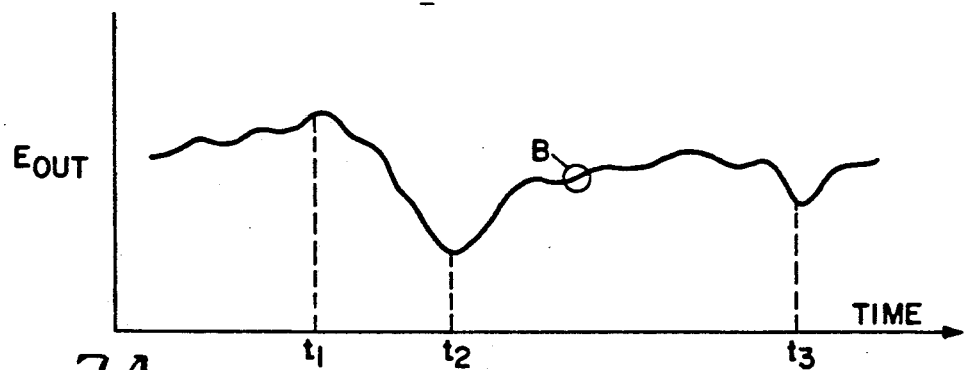
FIG. 3A is a waveform diagram illustrating representative fluctuations in the output signal from an oxygen sensor when such sensor is placed in the right atrium of a patient's heart, as shown in FIG. 2.

Referring next to FIG. 3A, a waveform diagram illustrating representative fluctuations in the output signal from the sensor 34 of FIG. 2 (when such sensor is placed in the right atrium 38 of a patient's heart 36) is illustrated. The horizontal axis in the diagram shown in FIG. 3A represents time, while the vertical axis represents the output signal, e.g., the output voltage, obtained from the sensor 34. As this output signal represents the optical reflectance properties of the blood, which properties are relatable to the oxygen content of the blood, the waveform shown in FIG. 3A thus depicts the variations in the oxygen content of the blood as a function of time.

The blood oxygen content measured in the right atrium of the patient's heart fluctuates as a function of time for two reasons: (1) there are different oxygen demands placed on the patient's body tissue at different times of the day depending upon the activities of the patient; and (2) different body tissue within the patient undergoes different oxygen demands because of the location of the body tissue. The first variation is a relatively slow variation, and may be considered as the average oxygen demand. At certain times of the day, such as when the patient is sleeping, the average oxygen demand is lowest. At other times of the day, such as when the patient is exercising, the average oxygen demand increases significantly. The second variation is a relatively fast variation, and occurs due to the fact that the blood returning to the right atrium from various body tissue locations is rather poorly mixed. Thoroughly mixed blood, from all body tissue locations, would not exhibit the second variation. However, because the blood is never thoroughly mixed in the right atrium, some of the second variation is always present.

In FIG. 3A, the first type of variation is predominantly illustrated. At time t!, for example, when the sensor output is high, the blood oxygen content is likewise high, indicating a time of relative inactivity of the patient. In contrast, at times t2 and t3, when the sensor output is low, the blood oxygen content is likewise low, indicating a time of relative activity of the patient.

Figure 3B:
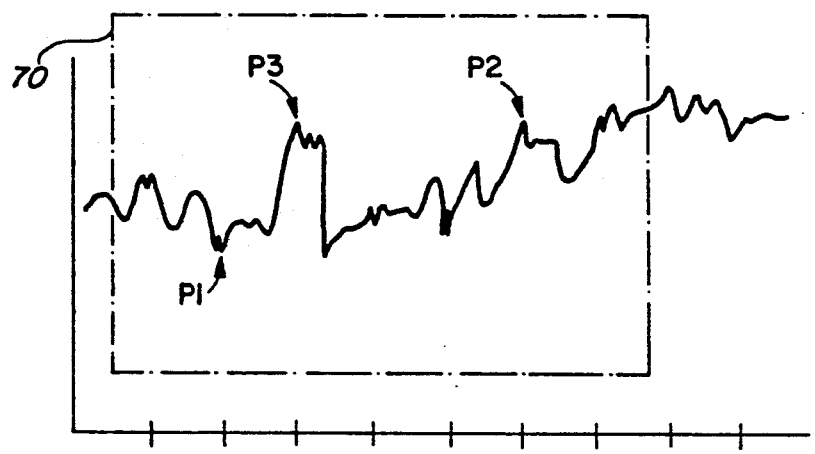
FIG. 3B is a waveform diagram of a small segment of the waveform in FIG. 3A, with an expanded horizontal (time) axis.

In FIG. 3B, the second type of variation is illustrated. That is, FIG. 3B depicts the type of variations in the blood oxygen measurement that may occur during a relatively short portion of the waveform of FIG. 3A, e.g., during the portion included within the circle B. As seen in FIG. 3B, such variations in the sensor output may be rather abrupt and sudden, evidencing the entry of blood into the right atrium from body tissue locations having markedly different oxygen content. A low sensor output, such as at the point P1, may be indicative of blood returning from a relatively active portion of the patient's body, such as an arm, where the oxygen demand of the body tissue is high. A high sensor output, such as at point P2, may be indicative of blood returning from a relatively inactive portion of the patient's body, such as the hip, where the oxygen demand of the body tissue is low. Alternatively, a high sensor output, such as at point P3, may be indicative of inappropriate reflection of light energy into the phototransistor of the sensor caused, e.g., by a moving heart valve.

In operation, the sensor 34 does not typically operate continuously (although it could with appropriate circuitry). That is, the sensor is typically energized during a refractory period of the heart and/or pacemaker circuits, and a "sample" of the blood oxygen content at that measurement time is made. Such sample times, i.e., those times when a measurement is made, are represented in FIG. 3B as heavy dots equally spaced along the horizontal axis. Statistically, assuming the fast variations in the blood oxygen content are more or less random, some of these sample times occur when the blood oxygen content is low, and others occur when it is high. Hence, within a particular measurement window 70, which "window" 70 includes a plurality of sample times, there will be one sample measurement that has a lower value than the others. In FIG. 3B, this low or minimum measurement is the one made at point P1. It is a feature of the present invention, to identify the low or minimum measurement within a given measurement window 70, and to use such measurement as an indicator of the relevant blood oxygen content, i.e., to use such minimum value as an indicator of the oxygen content of the blood returning from the body tissue undergoing the highest oxygen demand. This minimum value can then be used as a reliable indicator of the physiological need to adjust the heart rate, e.g., as controlled by a rate-responsive pacemaker.

It is to be noted that while FIG. 3B suggests that sample measurements made within the measurement window 70 be equally spaced in time, such equally spaced samples are not necessary. If sample measurements are taken, all that is necessary is that sufficient samples be obtained so that a statistically accurate minimum value will be obtained. (In contrast, if a continuous measurement is made, all that is required is that the minimum value of the blood oxygen content be determined for a prescribed measurement window.) For example, a plurality of discrete blood oxygen measurements could be made only during the refractory interval of a cardiac cycle. Such refractory interval may last, e.g., only 10–20 milliseconds during an 800 millisecond cardiac cycle. However, during this 10–20 milliseconds, several discrete measurements, e.g. 5–10, of the blood oxygen content can be measured. Alternatively, there is no requirement that the blood oxygen measurement be performed only during a refractory period. Thus, if desired, the blood oxygen measurement can be made at regular intervals throughout the cardiac cycle, either synchronous with the cardiac cycle, or asynchronous relative to the cardiac cycle.

Figure 4:
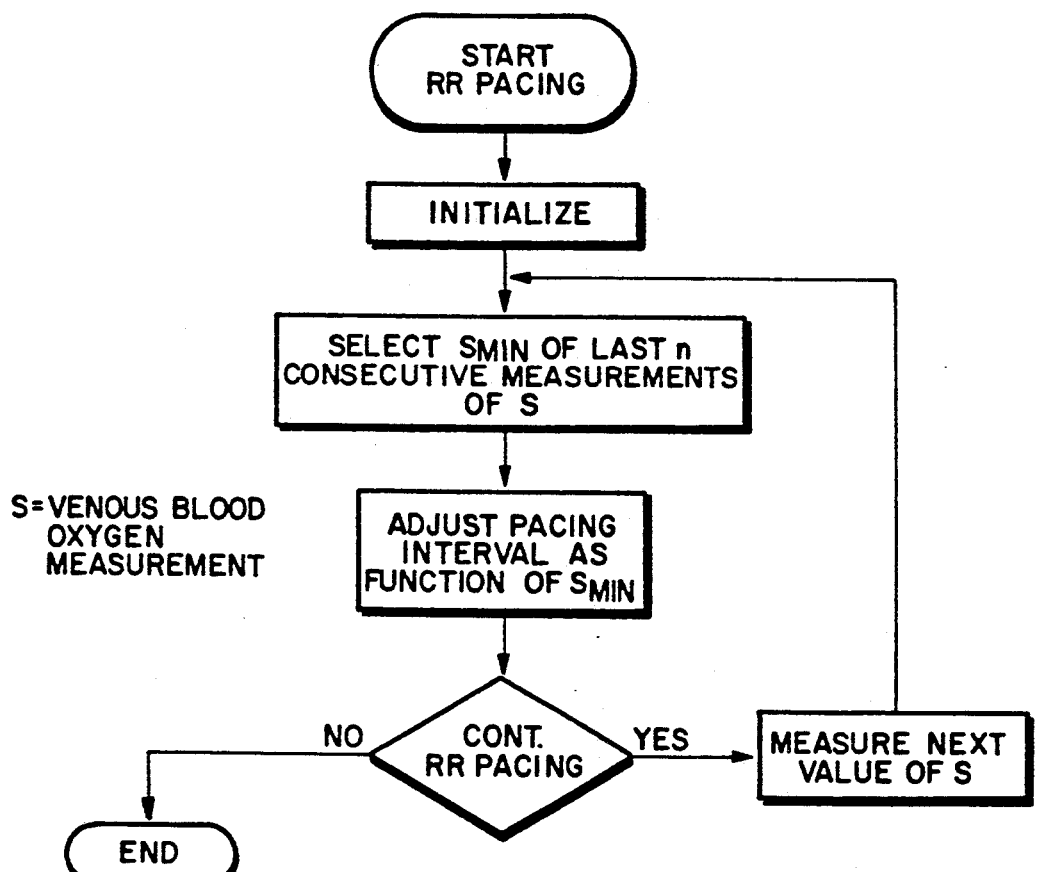
FIG. 4 is a simplified flow chart depicting a method of adjusting the pacing interval of a rate-responsive pacing system in accordance with one embodiment of the present invention.

FIG. 4 shows a simplified flow chart depicting one method of determining the minimum blood oxygen measurement and using this minimum blood oxygen measurement to automatically adjust the pacing interval of a rate-responsive pacing system. As seen in FIG. 4, once rate-responsive (RR) pacing has been started, an initialization step is performed. Such initialization step may involve, e.g., calibrating the blood oxygen sensor against a standard. Further, such step may involve assigning nominal values of blood oxygen measurement values until actual measurements of blood oxygen can be made. Once initialized, the minimum value of the last n (where n is an integer) consecutive blood oxygen measurements (where the term "S" is used in FIG. 4 to signify a blood oxygen measurement) is selected. This minimum value of S is then used as the control parameter to adjust the pacing interval of the pacemaker. If RR pacing is to continue, then the next value of S is measured and the process repeats.

To further illustrate the method depicted in FIG. 4, the following example is provided. Assume that twenty (n=20) consecutive measurements of S are to be made. Initialization of the method may thus involve assigning nominal values to represent the last 20 measurements. Once initialized, a first actual measurement is made. The minimum value of blood oxygen represented in this first actual measurement and 19 of the initialized nominal values is then selected as the control parameter for the RR pacing. A second blood oxygen measurement is then made. The minimum value of blood oxygen represented in the first and second actual blood oxygen measurements and 18 of the initialized nominal values is then selected as the control parameter for the RR pacing. This process continues until twenty actual measurements have been consecutively made and all twenty have been examined to determine the minimum blood oxygen measurement. Each time a new blood oxygen measurement is made, the oldest of the twenty most recent blood oxygen measurements is discarded. In this way, the minimum blood oxygen measurement is always selected from the twenty most recent measurements. The minimum blood oxygen measurement selected from the twenty most recent measurements will change only if the new blood oxygen measurement is less than the prior nineteen measurements.

It is to be understood that the above example is only one possible implementation of the method shown in FIG. 4. Any value of n could be employed, from vary small values (e.g., n =3) to very large values (e.g., n=100). Further, the value of n may be automatically changed by the RR pacing circuits at certain threshold levels. For example, at normal heart rates, when the patient is at rest, one value of n may be used. At higher heart rates, when the patient is exercising, a different value of n may be used.

Further, it is to be emphasized that the method shown in FIG. 4 is only one of several different types of methods or algorithms that may be used to select the minimum oxygen measurement. Any method of algorithm that systematically determines the minimum oxygen content measurement may be used.

Figure 5:
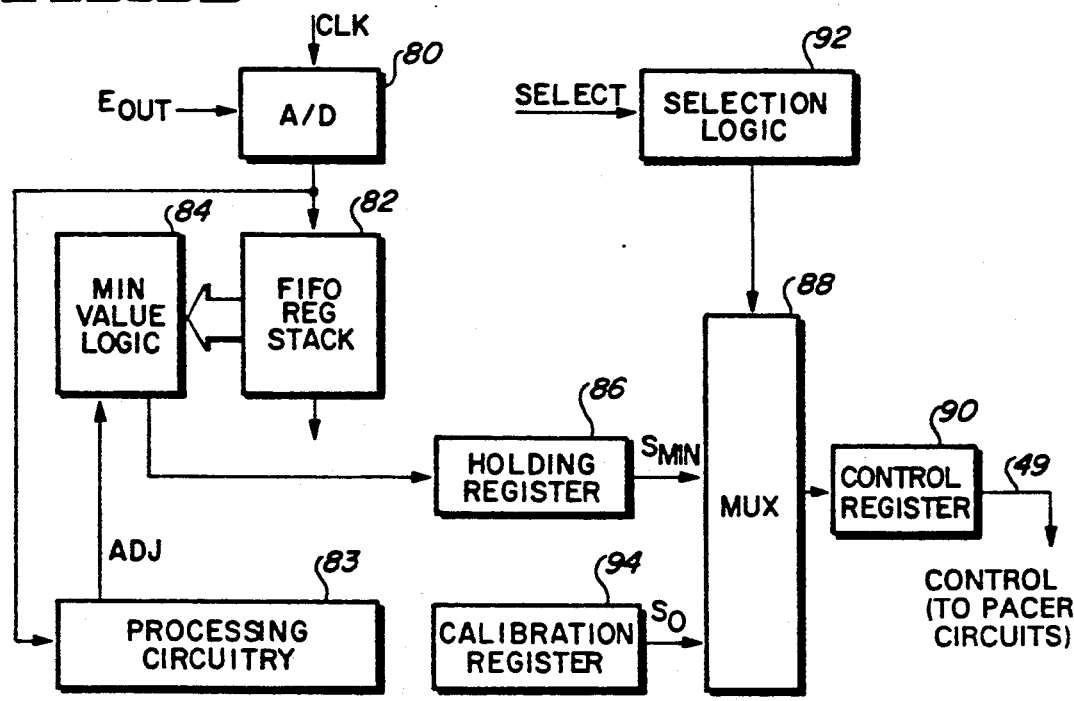
FIG. 5 is a simplified functional block diagram of the sensor process circuit of FIG. 2 made in accordance with a digital embodiment of the present invention.

Referring next to FIG. 5, a simplified functional block diagram of a digital embodiment of the sensor process circuit 44 of FIG. 2 is shown. Such embodiment can be readily incorporated into a digitally controlled rate-rate-responsive pacemaker. (It is noted that most modern pacemakers are digitally controlled, many involving the use of a microprocessor, or equivalent, to control the operation of the pacemaker in accordance with prescribed operating programs, which programs may be altered as required to suit the needs of a particular patient.)

As seen in FIG. 5, the output signal from the sensor 34, EOUT, is directed to an analog-to-digital (A/D) converter 80. The resulting digital output signal is stored in a first-in first-out (FIFO) register stack 82. The number of registers included in the FIFO register stack 82 may be selected to be any desired value, e.g., 32. The contents of the various registers within the FIFO stack 82 are compared in Minimum Value Logic circuitry 84. That is, circuitry 84 compares the contents of each register in the FIFO stack 82 and determines which one has the lowest or minimum value. This value is then selected and placed in a holding register 86. Further, during a calibration mode, as explained below, the circuitry 84 may be programmed to make an adjustment to the minimum value selected in order to compensate for variations that may occur over time to the sensor 34.

During normal rate-responsive operation, the value held in the holding register 86 is selected by a multiplexer (MUX) circuit 88 and placed in a control register 90. The rate-responsive pacing circuits 46 (FIG. 2) look to the control register 90 for the control parameter that sets or controls the rate-responsive pacing interval.

Still referring to FIG. 5, selection logic 92 is utilized to control the MUX 88. In addition to selecting the contents of the holding register 86, the MUX 88 may also select the contents of a calibration register 94. The calibration register 94 may have a fixed value loaded therein, or a programmed value loaded therein. If a programmed value is used, such may be loaded into the register 94 using conventional programming techniques known in the art. (See, e.g., U.S. Pat. No. 4,232,679 (Schulman) for a basic description of how an implantable medical device may be programmed using an external programmer.) Selection logic 92 is controlled by an appropriate select signal. This select signal may be a programmable command signal sent to the implantable pacemaker from a non-implantable programming device, in conventional manner. During calibration, i.e., when selection logic 92 selects the contents of the calibration register 94, processing circuitry 83 examines the measured blood oxygen to determine if the sensor 34 is functioning properly. As required, the processing circuitry makes programmed adjustments to the measurement value passing through the minimum value logic 84 in order to add or subtract an appropriate increment therefrom.

In operation, the calibration circuitry shown in FIG. 5 functions as follows. With the patient at rest, or at some other known and controlled level of activity, an attending physician or cardiologist generates an appropriate command to cause selection logic 92 to select the contents of the calibration register 94 as the control parameter that is loaded in the control register 90. In such calibration mode, the pacemaker is essentially a non-rate-responsive pacemaker. Hence, the physician has some control as to the patient's heart rate. Further, in the calibration mode, the contents of the calibration register can be programmably altered to any desired value. In the calibration mode, the blood oxygen sensor 34 measures the blood oxygen content, with the value of such measurements, after being digitized, being directed to processing circuitry 83. The processing circuitry 83 (which may be part of the processing circuitry of the pacemaker circuits 46, particularly when such circuits 46 include one or more microprocessors) then determines if, for the known level of activity and heart rate of the patient, the blood oxygen measurements are approximately where they should be. If not, the processing circuitry 83 instructs the minimum value logic 84 to make whatever adjustments are needed to bring the blood oxygen measurements to an appropriate level before such measurements are placed in the holding register 86. In this manner, the measured value of blood oxygen may be adjusted, as required, in order to compensate for changes that may occur in the sensor over time.

Initially, the contents of the registers in the FIFO register stack 82 are all loaded with a nominal value. However, as actual measurements of blood oxygen are made, the digital values corresponding to such measurements supplant the nominal values initially loaded. After a short time, all values held in the register stack 82 represent the most recent n measurements of blood oxygen, where n is number of registers in the FIFO register stack 82 that are used. In this manner, the minimum value logic 84 always looks to the most recent n measurements in order to determine the minimum value that is to be used in accordance with the present invention.

It is to be emphasized that that which is shown in FIG. 5 is functional, and numerous variations in the manner of calibration and operation could be readily performed by those skilled in the art.

Figure 6A:
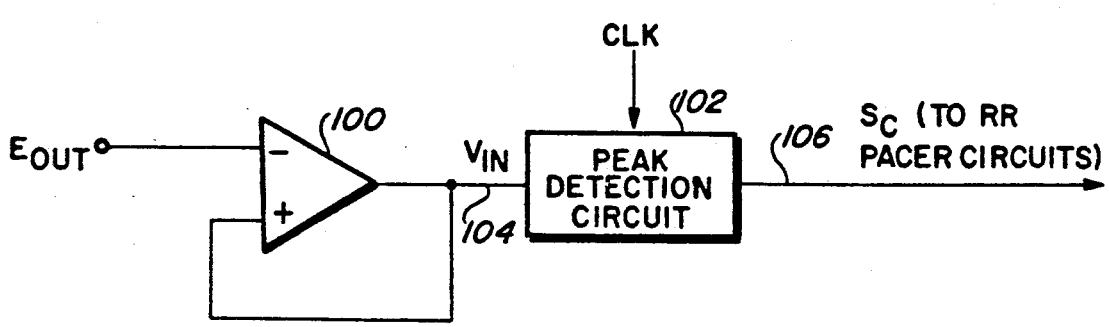
FIG. 6A is a simplified electrical schematic diagram of the sensor process circuit of FIG. 2 made in accordance with an analog embodiment of the present invention.
Figure 6B:
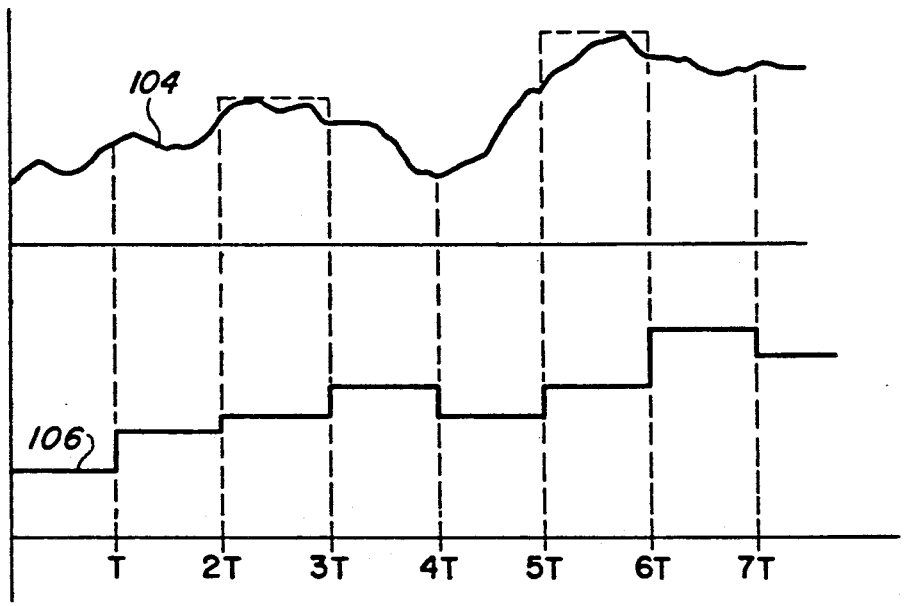
FIG. 6B is a timing waveform diagram illustrating the operation of the analog embodiment of FIG. 6A.

Referring next to FIG. 6A, a simplified electrical schematic diagram of an analog embodiment of the sensor process circuit 44 of FIG. 2 is shown, while FIG. 6B shows a timing waveform diagram illustrating the operation of the analog embodiment of FIG. 6A. In accordance with this embodiment, the output signal from the sensor 34 (FIG. 2) is directed to the inverting input of an input buffer amplifier 100. A peak detection circuit 102 then determines the peak of the input signal over a prescribed period of time, defined by a clock signal, and holds this value until the next period of time.

The inverse of the input waveform directed to the amplifier 100 is shown as the signal waveform 104 in FIG. 6B. Thus, the waveform 104 represents the input signal, VIN, directed to the peak detection circuit 102. While this signal is shown as a continuous signal (suggesting continuous operation of the sensor 34), it is noted that it need not be continuous. Rather, the sensor may be continuous for only a small portion of a cardiac cycle, with the signal waveform 104 representing that small portion; or, the sensor may be sampled at an appropriate rate, with the signal waveform 104 representing an extrapolated representation of the sampled signal. In either event, a clock signal, or equivalent, defines a time period T during which the waveform 104 is to be examined for a peak signal. (Note that a peak signal in the waveform 104 corresponds to a minimum signal in the output signal from the sensor 34, or a minimum blood oxygen measurement.) Once this peak signal has been found, it is held until the next period T.

To illustrate, in FIG. 6B, the waveform 104 is generally increasing during the first period T. The peak value of the waveform 104 occurs at the end of this first period. Thus, at the conclusion of T, the output signal, shown as the waveform 106 in FIG. 6B, assumes a value corresponding to the value of the waveform 104 at the end of period T. Similarly, during the second period which ends at 2T, the peak value of the waveform 104 occurs at the end of the second period. Thus, at the conclusion of 2T, the output signal 106 assumes a value corresponding to the value of the waveform 104 at the end of period 2T. During the third period, however, the peak of the signal 104 occurs somewhere near the start of the period. Thus, at the conclusion of the period 3T, the output waveform 106 assumes a value corresponding to this peak value. In a similar manner, the output waveform 106 assumes a value at the conclusion of each period corresponding to the peak value of the waveform 104 during that period. The output waveform 106 can then be used directly or indirectly (e.g., converted to a digital value) as a measure of the minimum oxygen content of the blood. As desired, such measure may also be used as the control parameter of a rate-responsive pacemaker.

Those skilled in the art will recognize that the circuit shown in FIG. 6A and described in connection with FIG. 6B is simply a peak detection and hold circuit, sometimes referred to as a "boxcar" circuit (because the shape of the output waveform 106 resembles the profile of boxcars of a passing train, each loaded with cargo of differing heights). Such circuit, or equivalent, may advantageously be used as part of the present invention in order to readily determine the minimum value of blood oxygen during a particular time interval.

Figure 6C:
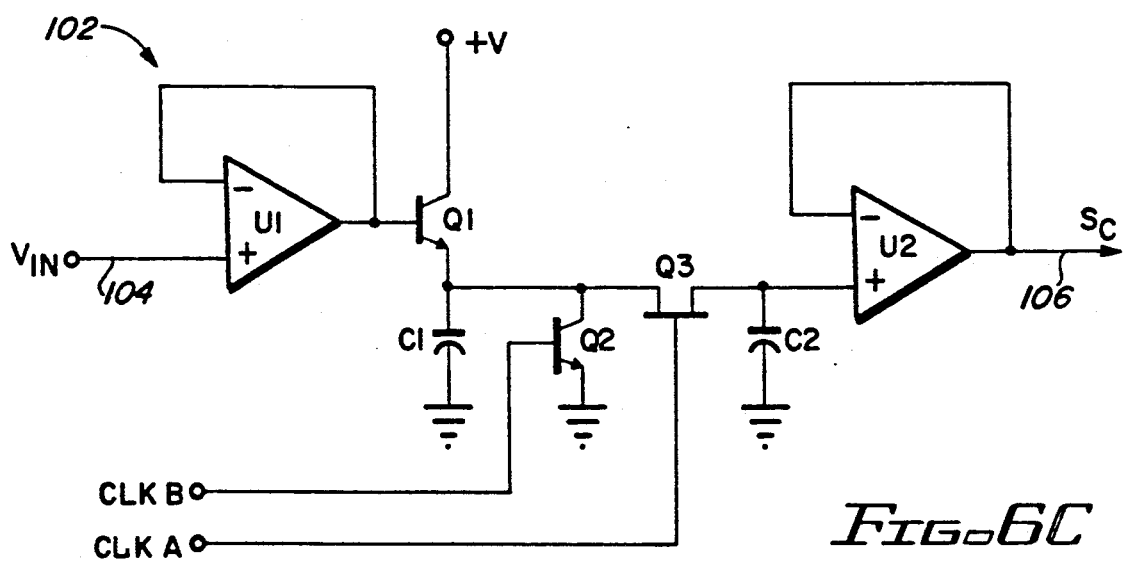
FIG. 6C shows one embodiment of the peak detection circuit of FIG. 6A.
Figure 6D:
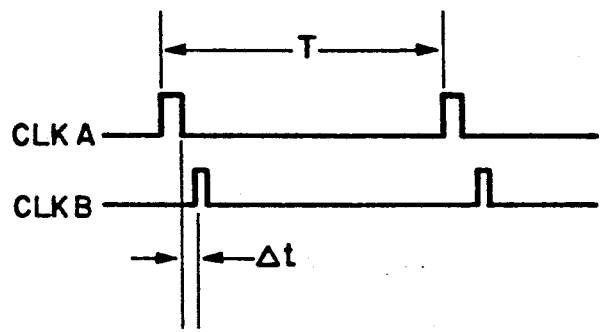
FIG. 6D is a timing diagram illustrating the relationship between the clock signals used in the peak detection circuit of FIG. 6C.

FIG. 6C shows an exemplary embodiment of the peak detection circuit of FIG. 6A; and FIG. 6D is a timing diagram illustrating the relationship between the clock signals used in the peak detection circuit of FIG. 6C. As seen in these figures, the peak detection circuit 102 includes an amplifier U1 driving an emitter follower Q1. The output of the emitter follower Q1 is coupled to a holding capacitor C1. As long as the output voltage of the amplifier U1 is rising, the voltage applied to the capacitor C1 follows. However, as soon as the output voltage of the amplifier U1 falls below the voltage on the capacitor C1, the emitter-base junction of the follower Q1 becomes back biased, thereby maintaining the prior voltage level on C1. At the appropriate time, e.g., at the end of the sample period, a switch Q3 is turned on by clock signal, CLK A, allowing the voltage on C! to be passed, through output amplifier U2, to the output signal line 106. A short time thereafter, another clock signal, CLK B, turns on switch Q2, causing the voltage held on capacitor C1 to be discharged to ground. This action thus clears capacitor C1 of is previous voltage, thereby allowing the voltage on capacitor C1 to seek the peak value of the input voltage for the next period.

FIG. 6D illustrates a preferred relationship between the clock signals CLK A and CLK B. CLK A defines the measuring period T. This clock may be obtained from the pacemaker circuits 46 (FIG. 2), or derived from an appropriate oscillator. For purposes of the present invention, the period T need not be precise. CLK B includes the same period as CLK A, but is delayed a slight amount, t, therefrom. The length of delay may be small, on the order of microseconds. Its purpose is simply to ensure that switch Q3 is turned OFF, after having been turned ON to present the output voltage to the amplifier U2, before the switch Q2 is turned ON to discharge capacitor C1.

As described above, it is thus seen that the present invention provides an accurate and reliable system and/or method for determining the oxygen content of venous blood using optical measuring techniques, i.e., emitting light energy into the blood and sensing the amount of light energy reflected therefrom, regardless of reflections and other erroneous light energy that may be present at the time a particular measurement is made. Such an accurate and reliable measuring system or method is realized by making many measurements, e.g., spaced close together in time, and discarding all the measurements but the one(s) evidencing the lowest oxygen content. Thus, while the sensing of any erroneous light energy, caused by reflections or otherwise, may adversely affect one or more individual measurements (causing such measurements to indicate a higher than actual oxygen content), such affected measurements are discarded and not considered.

As further described above, it is also seen that the present invention provides a reliable and accurate system and/or method for measuring the oxygen content of blood returning from body tissue undergoing the greatest oxygen demand, e.g., experiencing the most physical exercise, even though such blood is in the process of being mixed, e.g., in the right atrium, with blood returning from body tissue not experiencing a high oxygen demand. Advantageously, such system and/or method is again realized by making many measurements, e.g., spaced close together in time, and responding only to the minimum blood oxygen content measurement(s), and discarding or ignoring the non-minimum blood oxygen content measurements. The minimum blood oxygen measurement represents that portion of the poorly mixed blood having the lowest oxygen content, i.e., that blood from body tissue undergoing the greatest oxygen demand. In this way, the present invention advantageously provides a system and/or method that automatically determines or selects relevant blood oxygen measurements (i.e., from blood returning from active body tissue) from irrelevant blood oxygen measurements (i.e., from blood returning from non-active body tissue).

Moreover, as also described above, it is seen that the present invention provides a system and/or method for easily and accurately measuring relevant blood oxygen levels and using such measurements as a control parameter in a rate-responsive pacing system.

Finally, as further indicated above, the present invention provides a rate-responsive pacing system and/or method wherein stimulation pulses are provided to a patient's heart on demand at a rate that is determined by the oxygen content of blood returning from those parts of the patient's body experiencing the greatest oxygen demand.

While the invention herein disclosed has been described by means of specific embodiments and applications thereof, numerous modifications and variations could be made thereto by those skilled in the art without departing from the scope of the invention set forth in the claims.

What is claimed is:

1. A method of automatically controlling the rate at which a rate-responsive pacemaker delivers pacing pulses to a patient's heart, said method comprising the steps of:
(a) measuring the oxygen content of blood returning to the right atrium of the patient's heart as the blood enters the right atrium before the blood has an opportunity to become thoroughly mixed;
(b) determining the minimum value of blood oxygen content measured in step (a) during a prescribed time period, said prescribed time period including at least a portion of a plurality of consecutive cardiac cycles; and
(c) using the minimum value blood oxygen content determined in step (b) as a direct indicator of the blood oxygen content of the blood returning from body tissue of the patient, undergoing the highest oxygen demand, and hence as an indicator of the need to adjust the pacing rate of said rate-responsive packmaker.

2. The method of automatically controlling the rate of a rate-responsive pacemaker as set forth in claim 1, wherein step (a) includes measuring the blood oxygen content at a plurality of discrete times within said prescribed time period, and step (b) includes comparing the values of blood oxygen content evidenced by each of said plurality of discrete time measurements and selecting the one that evidences a minimum value of blood oxygen saturation.

3. The method of automatically controlling the rate of a rate-responsive pacemaker as set forth in claim 2, wherein step (a) includes converting each of the measurements of blood oxygen content to a digital value and saving the digital values corresponding to the most recent n measurements, where n is an integer, and wherein step (b) comprises selecting from said n saved digital values the one digital value that evidences a minimum value of blood oxygen saturation.

4. The method of automatically controlling the rate of a rate-responsive pacemaker as set forth in claim 3, wherein step (a) further includes continuing to measure the blood oxygen content at selected sample times to obtain an updated measurement, converting each such updated measurement to a digital value, and saving each updated digital value as one of said n saved digital values while discarding the one saved digital value corresponding to the oldest of the blood oxygen content measurements, whereby the number of saved digital values remains at n.

5. The method of automatically controlling the rate of a rate-responsive pacemaker as set forth in claim 4, wherein step (a) includes making said updated measurements at sample times determined relative to a cardiac cycle of said patient.

6. The method of automatically controlling the rate of a rate-responsive pacemaker as set forth in claim 4, wherein step (a) includes making said updated measurements at fixed increment sample times.

7. The method of automatically controlling the rate of a rate-responsive pacemaker as set forth in claim 1, wherein step (a) comprises converting the measurement of the blood oxygen content to a continuous analog signal wherein a peak value of a first polarity represents a minimum oxygen content, and wherein step (b) comprises detecting the maximum peak value of said analog signal of said first polarity during said prescribed time period.

8. The method of automatically controlling the rate of a rate-responsive pacemaker as set forth in claim 7, wherein step (b) includes monitoring said continuous analog signal for a prescribed number of cardiac cycles of said patient, thereby defining said prescribed time period as said prescribed number of cardiac cycles, and determining the maximum peak value of said analog signal of said first polarity during each occurrence of said prescribed number of cardiac cycles.

9. The method of automatically controlling the rate of a rate-responsive pacemaker as set forth in claim 7, wherein step (b) includes monitoring said continuous analog signal for a recurring fixed time period, thereby defining said prescribed time period as said fixed time period, and determining the maximum peak value of said analog signal of said first polarity during each of said fixed time periods.

10. A method of determining the physical activity level of a patient comprising:
(a) repeatedly measuring the oxygen content of blood in the right atrium of the patient's heart as the blood enters the right atrium before the blood has an opportunity to become thoroughly mixed;
(b) monitoring the measurements made in step (a) over a prescribed interval, said prescribed interval including at least a portion of a plurality of consecutive cardiac cycles;
(c) ascertaining the minimum blood oxygen content measured during the monitoring interval of step (b); and
(d) using the minimum blood oxygen content ascertained in step (c) as a direct indicator of the blood oxygen content of the blood returning from body tissue of the patient undergoing the greatest oxygen demand, and hence as a direct indicator of the body tissue experiencing the most physical exercise, the lower the minimum blood oxygen content the greater the physical activity.

11. The method of determining physical activity as set forth in claim 10, wherein step (a) comprises measuring the blood oxygen content at least once during each consecutive cardiac cycle.

12. The method of determining physical activity as set forth in claim 10, wherein step (a) comprises measuring the blood oxygen content at least once every n consecutive cardiac cycles, where n is an integer less than ten.

13. The method as set forth in claim 10 further including:
(e) using the minimum blood oxygen content measured in step (d) as a direct indicator of the need to adjust the rate of a rate-responsive pacemaker implantable in said patient.

14. A system for reliably determining the physical activity level of a patient comprising:
measurement means for repeatedly measuring the oxygen content of blood in the right atrium of the patient's heart before the blood has an opportunity to become thoroughly mixed;
monitoring means for monitoring the blood oxygen measurements made with said measurement means over a prescribed interval, said prescribed interval including at least a portion of a plurality of consecutive cardiac cycles; and
determining means for determining the minimum blood oxygen content measured during said prescribed interval, said minimum blood oxygen content measurement providing a direct indicator of the blood oxygen content of the blood returning from body tissue of the patient undergoing the greatest oxygen demand, and hence a direct indicator of the body tissue experiencing the most physical exercise, the lower the minimum blood oxygen content the greater the physical activity.

15. The system as set forth in claim 14, wherein said prescribed interval comprises the length of time required for said measurement means to perform n discrete measurements of said blood oxygen content, where n is an integer.

16. The system as set forth in claim 15, wherein said determining means includes a first-in first-out (FIFO) register stack into which said n discrete measurements are placed, and further includes means for examining the contents of said FIFO register stack to determine which measurement of all the measurements in said FIFO register stack represents said minimum blood oxygen content.

17. A rate-responsive pacing system comprising:
 a blood oxygen sensor, said sensor including light emitting means for emitting light energy from said blood oxygen sensor, and light sensing means for sensing light energy directed to said blood oxygen sensor;
 a sensor drive circuit for selectively energizing said light energy emitting means and causing said light emitting means to emit light energy;
 a sensor process circuit for determining the amount of light energy sensed by said light sensing means corresponding to a given amount of light emitted by said light emitting means, and for converting said determined amount of light energy into a first measurement representative of the minimum amount of said light energy sensed during a prescribed interval, said prescribed interval comprising at least a portion of a plurality of consecutive cardiac cycles;
 rate-responsive pacing means for generating stimulation pulses on demand at a rate controlled by said first measurement; and
 lead means for delivering said stimulation pulses to a desired heart chamber;
 said blood oxygen sensor being positioned for emitting and sensing light in the vicinity of venous blood in the right atrium of the heart before said venous blood has an opportunity to become thoroughly mixed;
 whereby the rate at which said pacing pulses arm provided to said desired heart chamber on demand is determined by the minimum amount of light energy sensed by said blood oxygen sensor during said prescribed interval, which minimum amount of light energy corresponds to the minimum amount of oxygen present in said venous blood during said prescribed interval, and which minimum amount of oxygen provides a direct indication of the blood oxygen in the venous blood returning from the body tissue of the patient undergoing the greatest oxygen demand.

18. The rate-responsive pacing system as set forth in claim 17, wherein said sensor drive circuit and said sensor process circuit make at least n discrete measurements of the blood oxygen during each cardiac cycle included within said prescribed interval, where n is an integer, and wherein said process circuit includes minimum value logic for determining the minimum value of the most recent n discrete measurements.

* * * * *